US010617624B2

United States Patent
Nijakowski

(10) Patent No.: US 10,617,624 B2
(45) Date of Patent: *Apr. 14, 2020

(54) METHODS FOR SMOOTHING WRINKLES AND SKIN TEXTURE IMPERFECTIONS

(71) Applicant: The Procter & Gamble Company, Cincinnati, OH (US)

(72) Inventor: Timothy Roy Nijakowski, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 192 days.

This patent is subject to a terminal disclaimer.

(21) Appl. No.: 15/450,269

(22) Filed: Mar. 6, 2017

(65) Prior Publication Data

US 2017/0172887 A1 Jun. 22, 2017

Related U.S. Application Data

(63) Continuation of application No. 14/865,146, filed on Sep. 25, 2015.

(60) Provisional application No. 62/055,805, filed on Sep. 26, 2014.

(51) Int. Cl.
| | | |
|---|---|---|
| *A61K 8/81* | (2006.01) |
| *A61Q 19/00* | (2006.01) |
| *A61K 8/87* | (2006.01) |
| *A61K 8/06* | (2006.01) |
| *A61K 8/34* | (2006.01) |
| *A61Q 19/08* | (2006.01) |
| *A61K 8/04* | (2006.01) |
| *A61K 8/49* | (2006.01) |
| *A61K 8/73* | (2006.01) |
| *A61K 8/67* | (2006.01) |

(52) U.S. Cl.
CPC ............ *A61K 8/8147* (2013.01); *A61K 8/042* (2013.01); *A61K 8/06* (2013.01); *A61K 8/345* (2013.01); *A61K 8/4926* (2013.01); *A61K 8/675* (2013.01); *A61K 8/73* (2013.01); *A61K 8/87* (2013.01); *A61Q 19/00* (2013.01); *A61Q 19/08* (2013.01); *A61K 2800/48* (2013.01); *A61K 2800/524* (2013.01); *A61K 2800/88* (2013.01)

(58) Field of Classification Search
None
See application file for complete search history.

(56) References Cited

U.S. PATENT DOCUMENTS

| | | |
|---|---|---|
| 2003/0215476 A1 | 11/2003 | Cassin |
| 2004/0136937 A1 | 7/2004 | Cassin |
| 2007/0166259 A1 | 7/2007 | Vicic |
| 2007/0224158 A1 | 9/2007 | Cassin |
| 2008/0181953 A1 | 7/2008 | Cassin |
| 2008/0187592 A1 | 8/2008 | Cassin |
| 2008/0248121 A1 | 10/2008 | Cassin |
| 2008/0305069 A1 | 12/2008 | Cassin |
| 2009/0269299 A1 | 10/2009 | Cassin |
| 2009/0285770 A1 | 11/2009 | Laboureau |
| 2010/0009931 A1 | 1/2010 | Laboureau |
| 2010/0203004 A1 | 8/2010 | Simonnet |
| 2013/0302385 A1 * | 11/2013 | Muenz ................ A61K 8/91 424/401 |
| 2016/0089323 A1 | 3/2016 | Nijakowski |
| 2016/0089324 A1 | 3/2016 | Nijakowski |

FOREIGN PATENT DOCUMENTS

| | | | |
|---|---|---|---|
| DE | 10 2014 225607 | 10/2015 |
| FR | 2872410 | 12/2006 |
| FR | 2924022 | 12/2009 |
| FR | 2925319 | 2/2010 |
| FR | 2927803 | 12/2010 |
| FR | 2927804 | 2/2011 |
| FR | 2953398 | 6/2011 |
| FR | 2954143 | 2/2012 |
| FR | 2973242 | 10/2012 |
| FR | 2892017 | 11/2012 |
| FR | 2992204 | 7/2014 |
| WO | WO-0117496 A1 * | 3/2001 | ............... A61K 8/31 |
| WO | WO200742679 | 6/2007 |
| WO | WO-2009056545 A1 * | 5/2009 | ............... A61K 8/25 |
| WO | WO2012130690 | 10/2012 |

OTHER PUBLICATIONS

"Innovation Zone Apr. 2014 pp. 1-72, Retrieved from the Internet: http://www.in-cosmetics.com/ Formulation Display—High Performance Oxygen Energizing Eye Gel with OxyForce Cellular Active"; Stand 3G70, Air Products & Chemicals Inc.; p. 44.
PCT International Search Report dated Dec. 2, 2015—12 pages.

* cited by examiner

*Primary Examiner* — H. Sarah Park
(74) *Attorney, Agent, or Firm* — C. Brant Cook

(57) ABSTRACT

A skin smoothing composition that has from about 0.5 to about 10%, by weight, of an interpenetrating polymer that is a co-polymer of polyurethane and a polyacrylic polymer. The composition further contains from about 0.1% to about 5%, by weight, of a thickener made from homopolymers of acrylic acid crosslinked with a cross linker selected from the group consisting of an allyl ether pentaerythritol, allyl ether of sucrose, allyl ether of propylene and mixtures thereof and from about 10 to 98% water.

12 Claims, 1 Drawing Sheet

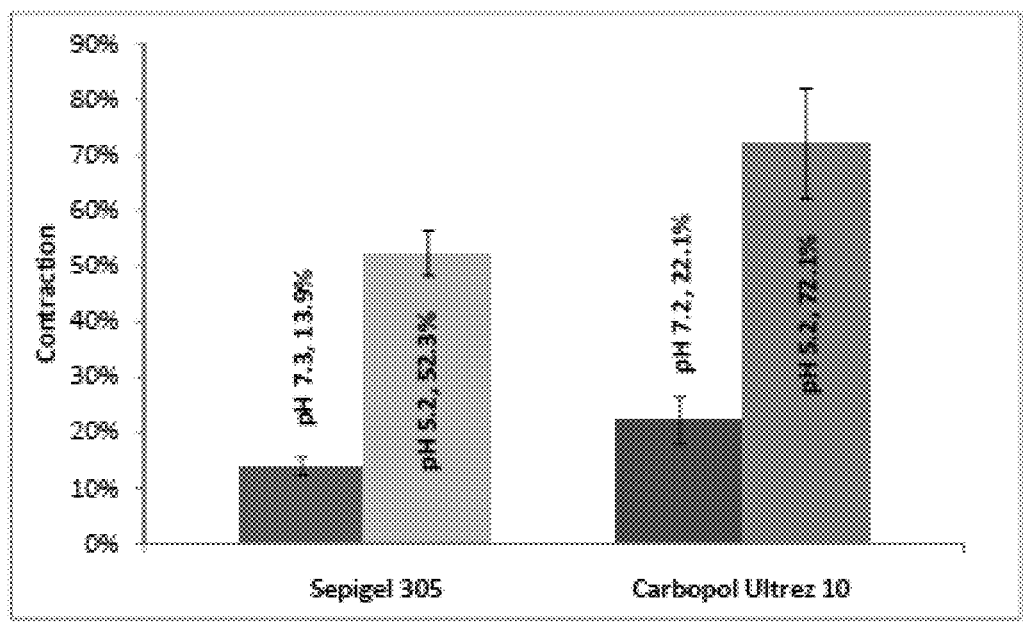

METHODS FOR SMOOTHING WRINKLES AND SKIN TEXTURE IMPERFECTIONS

FIELD OF THE INVENTION

The present invention relates to personal care compositions, and methods of use thereof, which exhibit adhesion and contraction of skin to smooth and flatten wrinkles and texture imperfections.

BACKGROUND OF THE INVENTION

Visible wrinkles, particularly those on the face and around the eyes, are one of the most prevalent and undesirable signs of aging. Many consumer products and procedures are devoted to hiding or reducing wrinkles. These products and procedures can be simple and inexpensive, for example, applying make-up, particularly a primer or colored foundation, to simply cover the wrinkles on a consumer's skin. Far more expensive and drastic procedures, such as surgical face lifts and Botox injections are also used to reduce the appearance of wrinkles on the face. There are a plethora of lotions and creams which purport to hydrate the skin making it more supple and reducing the appearance of wrinkles. Some of these liquid products contain active ingredients, for example niacinamide, that help repair and rejuvenate skin over time. All of these products and procedures have drawbacks.

Foundation and other make-up products are often visible, offer minimal texture benefits, and have no lasting effect on the skin. Once the make-up is removed, the skin is the same in appearance as before the make-up was applied. Liquid products can have chronic, acute or both effects on the skin. Hydration and optical effects are common acute benefits, and these benefits wear-off over time. Chronic actives may rejuvenate or repair the skin over time. These chronic benefits take time to occur and are incremental improvements. There are limits to how effective these chronic benefits can be. Plastic surgery and injections of chemicals have a more pronounced, immediate and dramatic effect on the look of a consumer's skin, but these procedures can be very expensive and come with many risks. Plastic surgery has the same risk of failure as any other surgical procedure, including disfigurement.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to skin and even contractile. Wrinkles, in their simplest form, are crevices or valleys in the skin. When an adhesive, contractile film former is applied, the skin at the bottom of the valley or crevice may be pulled to the surface, causing skin look smooth and wrinkle-free. The drawbacks of existing adhesive, contractile film forming products include discomfort caused by the contraction of the skin, irritation of the skin, cracking of the film as the consumer uses her face muscles, incompatibility with other cosmetic products in her regimen, and visibility of the film which is often whitish and noticeable. Curing or reducing one of these problems has, in the past, exacerbated one of the other problems.

Sodium silicate is an adhesive, contractile film forming ingredient used today. High levels of sodium silicate can result in high to moderate skin contraction, resulting in high to moderate immediate wrinkle reduction. Unfortunately, however, the more sodium silicate used, the more skin irritation observed and the more brittle (less durable) the dried film. One skilled in the art may attempt to use plasticizers to combat the problem of a brittle film, however, as stated above resolving this issue exacerbates others—in this case whiteness increases and contraction is reduced. Thus, these solutions are not acceptable to the consumer.

Thus, there is a continuing desire to provide compositions and methods of treatment that can improve the appearance of skin, more specifically, reduce the appearance of wrinkles on skin, while balancing the correct amount of skin contraction, film flexibility, lack of film whiteness, contraction resiliency, compatibility with other cosmetic products, and lack of skin irritation. These and other improvements over the art are provided by the present invention.

SUMMARY OF THE INVENTION

There is provided a skin smoothing composition that has from about 0.5 to about 10%, by weight, of an interpenetrating polymer comprising a co-polymer of polyurethane and a polyacrylic polymer, preferably a co-polymer of polyurethane-2 and polymethyl methacrylate, and even more preferably, a copolymer of neopentyl glycol/adipic acid/4,4'-methylenebis(cyclohexyl isocyanate)/dimethylolpropanoic acid and of polymethyl methacrylate. The composition further comprises from about 0.1% to about 5%, by weight, of a thickener comprising homopolymers of acrylic acid crosslinked with a cross linker selected from the group consisting of an allyl ether pentaerythritol, allyl ether of sucrose, allyl ether of propylene and mixtures thereof; and from about 10 to 98% water. The combination of a specific skin tightening, adhesive polymer and a specific type of thickener enhances the skin contraction and reduces the residual whiteness on the skin.

The compositions of the present invention can be combined in a kit with a second composition comprising at least one component selected from the group consisting of an oil-in-water emulsion, water-in-oil emulsion, thickened water gel, thickened oil phase, encapsulated oil phase, solid oil phase, and mixtures thereof, wherein the second composition is a skin care composition or colored cosmetic composition. The kits of the present invention preferably comprise instructions for complying with a regimen to provide a benefit to keratinous tissue.

In response to the technical problems identified in the Background of The Invention, the present invention provides compositions and kits that provide films with excellent initial and lasting contraction, are flexible, transparent, and non-irritating.

Further forms of the present invention will be appreciated in the detailed description that follows.

BRIEF DESCRIPTION OF THE FIGURE

The FIGURE illustrates the results of the comparative testing of Example 3.

DETAILED DESCRIPTION OF THE INVENTION

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a substrate such as the human skin surface or epidermis.

The term "dermatologically acceptable" as used herein means that the compositions or components described are suitable for use in contact with human skin tissue without undue toxicity, incompatibility, instability, allergic response, and the like.

The term "safe and effective amount" as used herein means an amount of a compound or composition sufficient to significantly induce a positive benefit.

The term "facial skin surface" as used herein refers to one or more of forehead, periorbital, cheek, perioral, chin, and nose skin surfaces. While facial skin surfaces are of concern and are exemplified herein, other skin surfaces may be treated with the compositions of the present invention, for example, surfaces typically not covered by clothing such as facial skin surfaces, hand and arm skin surfaces, foot and leg skin surfaces, and neck and chest skin surfaces (e.g., décolletage).

The terms "stable" and "stability" as used herein mean a composition which is substantially unaltered in chemical state, physical homogeneity and/or color when the composition is at a temperature of from about 1° C. to about 40° C.

Compositions

The present invention relates to various compositions and, more specifically, to compositions for application to a skin surface. The compositions may be in a wide variety of product forms that include, but are not limited to, solutions, suspensions, lotions, creams, gels, toners, sticks, pencil, sprays, aerosols, ointments, cleansing liquid washes and solid bars, pastes, foams, powders, mousses, wipes, strips, patches, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

Film Forming Composition

The skin smoothing compositions of this invention comprise from about 0.5 to about 10%, by weight, of an interpenetrating polymer comprising a co-polymer of polyurethane and a polyacrylic polymer, preferably a co-polymer of polyurethane-2 and polymethyl methacrylate, and even more preferably, a copolymer of neopentyl glycol/adipic acid/4,4'-methylenebis(cyclohexyl isocyanate)/dimethylolpropanoic acid and of polymethyl methacrylate. The composition further comprises from about 0.1% to about 5%, by weight, of a thickener comprising homopolymers of acrylic acid crosslinked with a cross linker selected from the group consisting of an allyl ether pentaerythritol, allyl ether of sucrose, allyl ether of propylene and mixtures thereof; and from about 10 to 98% water. Preferred film forming compositions form a non-tacky film which is removable with water used with cleansers such as soap. It is preferred the overall film forming composition has a pH of 5.4, more preferably from about 4.4 to about 6.4.

The preferred film forming compositions of the present invention are interpenetrating polymers (IPNs), in particular those comprising a polyurethane polymer and a polyacrylic polymer, such as the one prepared according to the process described in U.S. Pat. No. 5,173,526. Preferably, use may be made of an IPN of a polyurethane copolymer of neopentyl glycol/adipic acid/4,4'-methylenebis(cyclohexyl isocyanate)/dimethylolpropanoic acid and of polymethyl methacrylate, such as the product sold by the company AIR PRODUCTS under the trade name Hybridur® 875 polymer dispersion (INCl name: POLYURETHANE-2 (and) POLYMETHYL METHACRYLATE), or alternatively under the trade names Hybridur® 870 and Hybridur® 880;

In addition to the film forming polymers and thickeners of the present invention the film forming composition can optionally comprise additional film forming polymers. Examples of suitable optional film forming polymeric materials include:
a) sulfopolyester resins, such as AQ sulfopolyester resins, such as AQ29D, AQ35S, AQ38D, AQ38S, AQ48S, and AQ55S (available from Eastman Chemicals);
b) polyvinylacetate/polyvinyl alcohol polymers, such as Vinex resins available from Air Products, including Vinex 2034, Vinex 2144, and Vinex 2019;
c) acrylic resins, including water dispersible acrylic resins available from National Starch under the trade name "Dermacryl", including Dermacryl LT;
d) polyvinylpyrrolidones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, as well as other PVP polymers disclosed by E. S. Barabas in the Encyclopedia of Polymer Science and Engineering, 2 Ed. Vol. 17 pp. 198-257;
e) polyurethanes, including Polyderm PE-PA, available from Alzo International Inc.;
f) co-polymerized amido ester compounds, including Polyderm PPG-17, available from Alzo International Inc.;
g) acrylic latex dispersions;
h) high molecular weight silicones such as dimethicone and organic-substituted dimethicones, especially those with viscosities of greater than about 50,000 mPas;
i) high molecular weight hydrocarbon polymers with viscosities of greater than about 50,000 mPas;
j) polysaccharide gums such as xanthan gum, dehydroxanthan gum, cellulose derivatives, crosslinked-xanthan gum, hydroxypropyl xanthan gum, undecylenoyl xanthan gum, deacetylated xanthan gum, guar gum, cellulose gum, carrageenan, hydroxylpropyl methyl cellulose, and sodium carboxymethyl chitin;
k) organosiloxanes, including organosiloxane resins, fluid diorganopolysiloxane polymers and silicone ester waxes.

Examples of these optional polymers are found in PCT publication Nos. WO96/33689, published Oct. 31, 1996; WO97/17058, published May 15, 1997; and U.S. Pat. No. 5,505,937 issued to Castrogiovanni et al. Apr. 9, 1996, all incorporated herein by reference. Additional film forming polymers suitable for use herein include the water-insoluble polymer materials in aqueous emulsion and water soluble film forming polymers described in PCT publication No. WO98/18431, published May 7, 1998, incorporated herein by reference. Examples of high molecular weight hydrocarbon polymers with viscosities of greater than about 50,000 mPas include polybutene, polybutene terephthalate, polydecene, polycyclopentadiene, and similar linear and branched high molecular weight hydrocarbons.

Optional film forming polymers include organosiloxane resins comprising combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is methyl. Note that a small amount, up to 5%, of silanol or alkoxy functionality may also be present in the resin structure as a result of processing. The organosiloxane resins must be solid at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrofunctional or $SiO_2$ "Q" units, otherwise known as "MQ" resins as disclosed in U.S. Pat. No. 5,330,747, Krzysik, issued Jul. 19, 1994, incorporated herein by reference. In the present invention the ratio of the "M" to "Q" functional units is preferably about 0.7 and the value of n is 1.2. Organosiloxane resins such as these are commercially available such as trimethylsiloxysilicate/cyclomethicone D5 Blend available from GE Toshiba Silicone, Wacker 803 and 804 available from Wacker Silicones Corporation of Adrian Michigan, KP545 from Shin-Etsu Chemical and G. E. 1170-002 from the General Electric Company. In the present invention, by having film forming polymer mainly in the second layer, the film forming polymer will exist in a higher concentration at a localized area, and thereby forming a film of higher film intensity when applied to the skin, compared to the remainder of the composition. Such concentrated area of high film intensity provides improved adhesion of the entire composition to the skin. Namely, by providing the film forming polymer mainly in the second layer, the amount of film forming polymer included in the entire composition can be reduced, or if the same amount of film forming polymer is formulated in the second layer, an entire composition having improved adhesion is obtained. In a preferred embodiment, the content level of film forming polymer in the second layer is from about 0.1% to about 20%, preferably from about 0.5% to about 10%, more preferably from about 1% to about 8%.

Thickener

Useful for the present invention is a thickener. Thickeners can be used for solidifying solid water-in-oil form compositions of the present invention. When used, the thickener is kept to below about 15% of the composition. Preferably the thickener is present in the composition at from about 0.05% to about 12%, more preferably from about 0.1% to about 10%, by weight of the film forming composition. The thickeners useful herein are selected from the group consisting of fatty compounds, gelling agents, inorganic thickeners and mixtures thereof. The amount and type of thickeners are selected according to the desired viscosity and characteristics of the product. These characteristics may include a synergistic effect between the thickener and the film forming ingredients, thereby enhancing product/film adhesion, contraction, or flexibility, while decreasing whiteness.

Preferred thickeners for use in the present invention comprise the Carbopol® polymer family, which is based on crosslinked polyacrylic acid chemistry. The products are crosslinked at different levels providing a portfolio of functionally diverse performance options. Poly(acrylic acid) (PAA or Carbomer) is generic name for synthetic high molecular weight polymers of acrylic acid. They may be homopolymers of acrylic acid, crosslinked with an allyl ether pentaerythritol, allyl ether of sucrose or allyl ether of propylene.

Poly(acrylic acid) is formed from the following monomer:

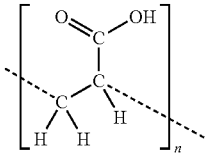

Optional additional thickening agents which can be used in the present invention include, polyacrylate copolymers such as SepiMAX ZEN (Seppic, Inc.); modified acrylate copolymers such as Sepiplus S (Seppic, Inc.) polymeric carboxylates including modified and unmodified starches, polysaccharide gums such as xanthan gum (e.g. CP Kelco's Keltrol CGT and Keltrol T630, Jungbunzlauer's Xanthan Gum), dehydroxanthan gum (e.g. Amaze XT from AkzoNobel), gallactomanan (Solagum Tara from Seppic), and cellulose derivatives (e.g. Natrosol 250). Gums may also include, but are not limited to, crosslinked-xanthan gum, hydroxypropyl xanthan gum, undecylenoyl xanthan gum, deacetylated xanthan gum, guar gum, cellulose gum, carrageenan, hydroxylpropyl methyl cellulose, and sodium carboxymethyl chitin.

Polymers useful herein include swellable, lightly to moderately crosslinked polyvinyl pyrrolidones (PVP) such as ACP-1120 (International Specialty Products), acrylate copolymers/crosspolymers/blends such as acrylate/steareth-20 itaconate copolymer (Structure 2001 from AkzoNobel), acrylates/C10-30 alkyl acrylates copolymer (Amaze XT from AkzoNobel), acrylic acid/VP crosspolymer (Ultrathix P100 from International Specialty Products).

Fatty compounds useful herein include stearic acid, palmitic acid, stearyl alcohol, cetyl alcohol, behenyl alcohol, stearic acid, palmitic acid, the polyethylene glycol ether of stearyl alcohol or cetyl alcohol having an average of about 1 to about 5 ethylene oxide units, and mixtures thereof. Preferred fatty compounds are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

The gelling agent useful as thickeners of the present invention include esters and amides of fatty acid gellants, hydroxy acids, hydroxy fatty acids, other amide gellants, and crystalline gellants. N-acyl amino acid amides useful herein are prepared from glutamic acid, lysine, glutamine, aspartic acid and mixtures thereof.

Plasticizer

The compositions of this invention may comprise at least one plasticizer present in the composition at from about 1% to about 20%, preferably from about 1% to about 15%, more preferably 2% to about 10% by weight. The plasticizer can be, for example, an alkyl mono-glycol or di-glycol containing 3 to 5 carbon atoms. Further the plasticizer can be propylene glycol. The plasticizers herein are selected from the group consisting of polyhydric alcohols, water soluble alkoxylated nonionic polymers, and mixtures thereof. Polyhydric alcohols useful herein include glycerin, propylene glycol, 1,3-butylene glycol, 1,3 propanediol, dipropylene glycol, diglycerin, sodium hyaluronate, polypropanediol and mixtures thereof.

Commercially available plasticizers herein include: glycerin available from Asahi Denka; propylene glycol with tradename LEXOL PG-865/855 available from Inolex, 1,2-PROPYLENE GLYCOL USP available from BASF; 1,3-butylene glycol available from Kyowa Hakko Kogyo; dipropylene glycol with the same tradename available from BASF; 1,3 propane diol with tradename ZEMEA from DuPont Company; polypropanediol with tradename CERENOL H250 from DuPont Company: diglycerin with tradename DIGLYCEROL available from Solvay GmbH; sodium hyaluronate with tradename ACTIMOIST available from Active Organics, AVIAN SODIUM HYALURONATE series available from Intergen, HYALURONIC ACID Na available from Ichimaru Pharcos.

Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, suspensions, and solid forms (e.g., gels, sticks, flowable solids, or amorphous materials). In certain embodiments, the dermatologically acceptable carrier is in the form of an emulsion or suspension. Emulsion or suspension may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. Nos. 3,755,560, 4,421,769, and *McCutcheon's Detergents and Emulsifiers*, North American Edition, pages 317-324 (1986). Suitable emulsions may have a wide range of viscosities, depending on the desired product form. The carrier may further comprise a thickening agent as are well known in the art to provide compositions having a suitable viscosity and rheological character.

Pigments and Powders

The compositions of the present invention can comprise from about 5% to about 45%, preferably from about 5% to about 30% of a pigment powder component. The pigments included in the pigment powder component herein may be hydrophobic in nature, or hydrophobically treated. By keeping the level of pigment component low, the entire composition maintains flexibility to accommodate other components which provide spreadability, moisturization, and fresh and light feel. The species and levels of the pigments are selected to provide, for example, shade, coverage, good wear performance, and stability in the composition. Pigments useful for the pigment component herein are inorganic and organic powder such as talc, mica, sericite, synthetic fluorphlogopite, pearl pigments such as alumina, barium sulfate, calcium secondary phosphate, calcium carbonate, coverage titanium oxide, finely divided titanium oxide, zirconium oxide, normal particle size zinc oxide, hydroxy apatite, iron oxide, iron titanate, ultramarine blue, Prussian blue, chromium oxide, chromium hydroxide, cobalt oxide, cobalt titanate, titanium oxide coated mica; organic powder such as polyester, polyethylene, polystyrene, methyl methacrylate resin, cellulose, 12-nylon, 6-nylon, styrene-acrylic acid copolymers, polypropylene, vinyl chloride polymer, tetrafluoroethylene polymer, boron nitride, fish scale guanine, laked tar color dyes, and laked natural color dyes. Such pigments may be treated with a hydrophobical treatment agent, including: silicone such as methicone, dimethicone, and perfluoroalkylsilane; fatty material such as stearic acid and disodium hydrogenated glutamate; metal soap such as aluminium dimyristate; aluminium hydrogenated tallow glutamate, hydrogenated lecithin, lauroyl lysine, aluminium salt of perfluoroalkyl phosphate, and aluminium hydroxide as to reduce the activity for titanium dioxide, and mixtures thereof. Such pigments may also be coated with substances considered more hydrophilic such as polysaccharides, caprylyl silane, or polyethylene oxide silane treatments.

Commercially available pigment powder component includes coverage titanium dioxide, such as SI-T-CR-50Z, SI-Titanium Dioxide IS, SA-Titanium Dioxide CR-50, SI-FTL-300 and SA/NAI-TR-10, all of them are available from Miyoshi Kasei, iron oxide and cyclopentasiloxane and dimethicone and disodium hydrogenated glutamate: SA/NAI-Y-10/D5(70%)/SA/NAI-R-10/D5(65%)/SA/NAI-B-10/D5 (75%) available from Miyoshi Kasei, iron oxide and disodium hydrogenated glutamate: SA/NAI-Y-10/SA/NAI-R-10/SA/NAI-B-10 available from Miyoshi Kasei, iron oxide and methicone: SI Mapico Yellow Light Lemon XLO/SI Pure Red Iron Oxide R-1599/SI Pure Red Iron Oxide R-3098/SI Pure Red Iron Oxide R-4098/SI Black Iron Oxide No. 247 available from Daito Kasei, alumina and titanium dioxide and methicone: SI-LTSG30AFLAKE H (5%) LHC available from Miyoshi Kasei, talc and methicone: SI-Talc JA13R LHC available from Miyoshi Kasei, mica and methicone: SI Mica available from Miyoshi Kasei, dimethicone: SA-SB-300 available from Miyoshi Kasei, mica and methicone: SI Sericite available from Miyoshi Kasei, mica and dimethicone: SA Sericite available from Miyoshi Kasei, mica and C9-15 Fluoroalcol Phosphates and Triethoxy Caprylylsilane: FOTS-52 Sericite FSE available from Daito Kasei, Talc and C9-15 Fluoroalcol Phosphates and triethoxy caprylylsilane: FOTS-52 Talc JA-13R available from Daito Kasei, boron nitride and methicone: SI02

Boron Nitride SHP-6 available from Daito Kasei, boron nitride and C9-15 fluoroalcol phosphates and triethoxy caprylylsilane: FOTS-52 Boron Nitride available from Daito Kasei, mica and titanium dioxide and methicone: SI Sericite TI-2 available from Miyoshi Kasei, mica and titanium dioxide and methicone: SI Mica TI-2 available from Miyoshi Kasei, talc and titanium dioxide and methicone: SI Talc TI-2 available from Miyoshi Kasei, lauroyl lysine: AMIHOPE LL available from Ajinomoto, synthetic fluorphlogopite and methicone: PDM-5L(S)/PDM-10L(S)/PDM-20L(S)/PDM-40L(S) available from Topy Industries.

Adhesive Agents

The compositions of the present invention can comprise from about 0.1% to about 10%, preferably from about 0.1% to about 2% of an adhesive agent. The species and levels of the adhesive agents are selected to provide, for example, a more flexible, longer-lasting benefit to composition, and/or better compatibility with other skin care or cosmetic formulations.

Examples of suitable adhesive agents include polyurethanes, including Polyderm PE-PA, available from Alzo International Inc.; co-polymerized amido ester compounds, including Polyderm PPG-17, available from Alzo International Inc.; and Acrylic Latex Dispersions.

Skin Active Agents

The compositions of the present invention may comprise a skin active agent which provides a particular skin care benefit characteristic of the usage of the skin care product. Herein, skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anaesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, hair growth inhibitors, desquamation enzyme enhancers, anti-glycation agents, and mixtures thereof. When included, the present composition comprises from about 0.001% to about 20%, preferably from about 0.1% to about 10% of at least one skin active agent.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™, available from Seppic Inc.

Skin lightening agents useful herein refer to active ingredients that improve hyperpigmentation as compared to pretreatment. Useful skin lightening agents herein include ascorbic acid compounds, vitamin $B_3$ compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

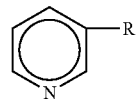

wherein R is —$CONH_2$ (e.g., niacinamide) or —$CH_2OH$ (e.g., nicotinyl alcohol); derivatives thereof and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and more preferred is niacinamide. In a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. Commercially available vitamin $B_3$ compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example available from Roche Vitamins), ascorbyl dipalmitate (for example, NIKKOL CP available from Nikko Chemical); undecylenoyl phenyl alanine (for example, SEPIWHITE MSH available from Seppic); octadecenedioic acid (for example, ARLATONE DIOIC DCA available from Uniquema); *Oenothera biennis* sead extract, and pyrus malus (apple) fruit extract, Water and Myritol 318 and butylene glycol and tocopherol and sscorbil tetraisopalmitate and Paraben and Carbopol 980 and DNA/

SMARTVECTOR UV available from COLETICA, magnesium ascorbyl phosphate in hyaluronic filling sphere available from COLETICA, and mixtures thereof.

Other skin active agents useful herein include those selected from the group consisting of N-acetyl D-glucosamine, panthenol (e.g., DL panthenol available from Alps Pharmaceutical Inc.), tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate: DL-α-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof. In a preferred example, the content level of a skin active agent is from about 0.001% to about 20%, more preferably from about 0.1% to about 10%.

Optional Components

The compositions hereof may further contain additional components such as those conventionally used in topical products, e.g., for providing aesthetic or functional benefit to the composition or skin, such as sensory benefits relating to appearance, smell, or feel, therapeutic benefits, or prophylactic benefits (it is to be understood that the above-described required materials may themselves provide such benefits).

These components may include, but are not limited to, materials purported to smooth, firm or lift sagging or wrinkled skin including: Quicklift, available from BASF Chemical Company; Syntran PC5100, available from Interpolymer Corporation; Glycolift, available from Solabia USA Inc.; Alguard, available from Frutarom; Easyliance, from Soliance; and Phytodermina Lifting code 9002, available from Istituto Ricerche Applicate.

The CTFA Cosmetic Ingredient Handbook, Second Edition (1992) describes a wide variety of nonlimiting cosmetic and pharmaceutical ingredients commonly used in the industry, which are suitable for use in the topical compositions of the present invention. Such other materials may be dissolved or dispersed in the composition, depending on the relative solubilities of the components of the composition.

UV Protection Powder

UV protection powder provides UV protection benefit in the composition. UV protection powder has a particle size of less than 100 nm, which size provide very little coverage effect to the skin. The composition of each layer of the present invention may comprise from about 0% to about 20%, preferably from about 0.1% to about 10% of a UV protection powder, such as micronized titanium dioxide and micronized zinc oxide. The powder included in the pigment component herein is typically hydrophobic in nature, or hydrophobically treated.

Commercially available UV protection powder is titanium dioxide and methicone SI-TTO-S-3Z available from Miyoshi Kasei, titanium dioxide and dimethicone and aluminum hydroxide and stearic acid: SAST-UFTR-Z available from Miyoshi Kasei, Zinc oxide: Finex series available from Sakai Chemical Industry.

UV Absorbing Agent

The compositions of the present invention may comprise a safe and effective amount of a UV absorbing agent. A wide variety of conventional UV protecting agent are suitable for use herein, such as those described in U.S. Pat. No. 5,087,445, Haffey et al, issued Feb. 11, 1992; U.S. Pat. No. 5,073,372, Turner et al, issued Dec. 17, 1991; U.S. Pat. No. 5,073,371, Turner et al., issued Dec. 17, 1991; and Segarin, et al, at Chapter VIII, pages 189 et seq., of Cosmetics Science and Technology (1972). When included, the present composition comprises from about 0.5% to about 20%, preferably from about 1% to about 15% of a UV absorbing agent.

UV absorbing agent useful herein includes, for example, 2-ethylhexyl-p-methoxycinnamate (commercially available as PARSOL MCX), butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, Eusolex™ 6300, Octocrylene, Avobenzone (commercially available as Parsol 1789), and mixtures thereof.

Radiant Powder

Radiant powder is a pigment that is particularly effective in providing radiant look to the skin, by having a gloss level of more than 7.0. Gloss level is a parameter which can be measured by a known method using the opacity charts available from THE LENETA COMPANY, Drawdown bar (0.003 μm and 0.006 μm), solvent (KP-545 available from Shin-Etsu Chemical Co., Ltd.), Gloss Checker IG-320 available from HORIBA.

The radiant powder useful herein includes pearl pigments, such as mica and titanium dioxide and dimethicone: SA-Timiron MP-1001 and SA-Flamenco Orange available from Miyoshi Kasei, Titanium Dioxide and Mica and Alumina and Silica and Demethicone/Methicone Copolymer and Iron Oxide: Relief Color Pink P-2 available from CATALYSTS & CHEMICALS IND. CO., LTD., mica, synthetic mica, boron nitride and specified particle talc having an average particle size of about 20 μm and a gloss level of about 7.2 (0.003 μm on white back), 33.0 (0.006 μm on white back), about 8.5 (0.003 μm on black back) and about 10.3 (0.006 μm on black back). Specified particle talc has a higher gloss level and a lower transparency level than normal particle talc. Specifically, the gloss level of specified particle talc is about 130% to 200% vs. normal particle talc and the transparency level of specified particle talc is about 10% to 100% vs. normal particle talc. Transparency level can be measured by a known method using the opacity charts available from THE LENETA COMPANY, Drawdown bar (0.003 μm and 0.006 μm), solvent (KP-545 available from Shin-Etsu Chemical Co., Ltd.), Spectraflash available from Datacolor. Commercially available specified particle talc is available from Miyoshi Kasei Inc. under the trade name of SI-TALC CT-20.

In a single layer formulation, because other powders, such as coverage titanium dioxide, contained in the formulation may overwhelm the radiant powder effect, to achieve the radiant look effect, a typical level of radiant powder is as high as 5%. In the present invention, by formulating the radiant powder mainly in the second layer and coverage titanium dioxide in the first layer, and providing the first and second layers in a manner such that they can be simultaneously applied on the skin, the skin care product of the present invention can provide satisfied radiant appearance effect with lower level of radiant powder. As a result, there is provided more flexibility in product formulation. Compared to a single layer product, a multiple layer product comprising lower level of radiant powder has a better spreadability and light feel on the skin. In a preferred example, the content level of radiant powder in the second layer is from about 5% to about 25%, more preferably from about 10% to about 20% by weight of the composition of the second layer. When calculated based on the total weight of the first layer and the second layer, the preferred content level of radiant powder is from about 0.5% to about 5%.

Soft Focus Powder

Soft focus powder is a pigment that is particularly effective in providing a soft focus effect to the composition, namely natural finish yet having good coverage for minimizing the appearance of skin troubles, when incorporated in a defined amount. Specifically, the soft focus powder herein must meet two parameter criteria to provide such an effect. First, both the Total Luminous Transmittance (Tt) and Diffuse Luminous Transmittance (Td) of the pigment are relatively high. The soft focus powder has a Total Luminous Transmittance (Tt) of from about 40 to about 94 and a Diffuse Luminous Transmittance (Td) of from about 28 to about 38. Without being bound by theory, it is believed that, by having such high Tt and Td values, the soft focus powder exhibits a high transparency, thereby providing an overall natural finish. Second, the soft focus powder has a relatively high Haze value {(Td/Tt)×100} of from about 32 to about 95. Without being bound by theory, it is believed that, by having such high Haze value, the contrast between lighted area of the skin and shaded area of the skin (such as pores and wrinkles) is minimized for reducing the appearance of the trouble areas.

Total Luminous Transmittance (Tt), Diffuse Luminous Transmittance (Td), and Haze value {(Td/Tt)×100} can be measured and calculated by the artisan by reference to ASTM D 1003-00 "Standard Test Method for Haze and Luminous Transmittance of Transparent Plastics". Although the pigments herein are not plastics, the same principles of this specific standard test can be applied.

The soft focus powder useful herein includes polymethyl/methacrylate (PMMA), silica, hybrid pigments such as alumina treated mica, titanium dioxide treated talc, titanium dioxide treated mica, vinyl dimethicone/methicone silsesquioxane crosspolymer, alumina, barium sulfate and synthetic mica. Commercially available soft focus powder useful herein includes alumina treated mica having the trade name SA Excel Mica JP2 available from Miyoshi Kasei, which has a Total Luminous Transmittance (Tt) of about 87, Diffuse Luminous Transmittance (Td) of about 28, and Haze value {(Td/Tt)×100} of about 32.

Similar to radiant powder, when formulated with coverage titanium dioxide in a single layer, the content level of a soft focus powder shall be as high as 5% to achieve noticeable natural look effect. However, in the present invention, by formulating soft focus powder mainly in the second layer and coverage titanium dioxide in the first layer, and providing the first and second layers in a manner such that they can be simultaneously applied on the skin, the skin care product of the present invention can provide satisfied natural look effect with relatively low level of soft focus powder. As a result, the cost of the product can be controlled while also providing more flexibility in product formulation. In a preferred example, the content level of soft focus powder in the second layer is from about 2% to about 25%, more preferably from about 5% to about 20% based on the composition of the second layer. When calculated on the basis of the total weight of the first layer and the second layer, the preferred content level of soft focus powder is from about 0.5% to about 4%, more preferably from about 1% to about 3%.

Silicone Elastomer

Soft focus silicone elastomer is crosslinked siloxane elastomer which is particularly effective in providing soft focus effect to the skin. In other words, when incorporated in a cosmetic product a defined amount of silicone elastomer, the silicone elastomer can provide natural finish yet having good coverage for minimizing the appearance of skin troubles. Specifically, silicone elastomer has lower matte level compared with other silicone oil. Matte level is a parameter reflecting soft focus effect, i.e. natural finish of a cosmetic material. The lower the matte level is, the better natural finish the material can provide. Matte level of silicone elastomer used in the present application is less than about 40. Matte level can be measured by the PG-1M gloss meter (Incidence angle/Reflection angle: 60/60°) made by Nihon Denshoku Kogyo. Commercially available silicone elastomer useful in the present application includes a silicone elastomer having the tradename KSG-16 available from Shinetsu, which has a matte level of about 37.

Silicone elastomer suitable for use herein can be emulsifying or non-emulsifying crosslinked siloxane elastomer or mixtures thereof. The term "non-emulsifying" as used herein, defines crosslinked organopolysiloxane elastomer from which polyoxyalkylene units are absent. The term "emulsifying" as used herein, means crosslinked organopolysiloxane elastomer having at least one polyoxyalkylene (e.g., polyoxyethylene or polyoxypropylene) unit. Non-emulsifying elastomer useful in the present invention is formed via crosslinking organohydroenpolysiloxane with an alpha, omega-diene. Emulsifying elastomer herein includes polyoxyalkylene modified elastomer formed via crosslinking from organohydrogenpolysiloxane with polyoxyalkylene diene or organohydrogenpolysiloxane containing at least one polyether group crosslinked with an alpha, omega-diene. Emulsifying crosslinked organopolysiloxane elastomer can notably be chosen from the crosslinked polymer described in U.S. Pat. Nos. 5,412,004, 5,837,793, and 5,811, 487. In addition, an emulsifying elastomer comprised of dimethicone copolyol crosspolymer (and dimethicone) is available from Shin Etsu under the tradename KSG-21.

Non-emulsifying elastomer is dimethicone/vinyl dimethicone crosspolymer. Such dimethicone/vinyl dimethicone crosspolymer is supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomer). Cross-linked organopolysiloxane elastomer useful in the present invention and processes for making them are further described in U.S. Pat.

Nos. 4,970,252, 5,760,116, and 5,654,362. Additional cross-linked organopolysiloxane elastomer useful in the present invention is disclosed in Japanese Patent Application JP 61-18708, assigned to Pola Kasei Kogyo KK. Commercially available elastomer preferred for use herein is Dow Corning's 9040 silicone elastomer blend, Shin Etsu's KSG-21, and mixtures thereof.

Similar to the radiant powder, when formulated with coverage titanium dioxide in a single layer, the content level of a silicone elastomer shall be as high as 10% to achieve noticeable natural look effect. However, in the present invention, by formulating a silicone elastomer mainly in the second layer and coverage titanium dioxide in the first layer, and providing the first and second layers in a manner such that they can be simultaneously applied on the skin, the skin care product of the present invention can provide satisfied natural look effect with lower level of silicone elastomer. As a result, the cost of the product can be controlled while also providing more flexibility in product formulation. In a preferred example, the content level of silicone elastomer in the second layer is from about 1% to about 20%, preferably from about 2% to about 15%. When calculated based on the total weight of the first layer and the second layer, the preferred content level of silicone elastomer is from about 0.5% to about 8%, more preferably from about 1% to about 5%.

Oil Absorbing Powder

Oil absorbing powder is a pigment that is particularly effective in absorbing oil, and thereby can be included in the present composition for absorbing excessive sebum from the skin. Specifically, the oil absorbing powder herein has an oil absorbency of at least about 100 mf/100 g, preferably at least about 200 mf/100 g. Oil absorbency is a unit well known to the artisan, and which can be measured via: HS K5101 No. 21 "Test Method for Oil Absorbency Level".

Oil absorbing powder useful herein includes spherical silica, and methyl methacrylate copolymer. Commercially available spherical oil absorbing pigments useful herein include spherical silica with tradename SI-SILDEX H-52 available from Miyoshi Kasei, Inc. having an oil absorbency of more than 200 mf/100 g, vinyl dimethicone/methicone silsesquioxane crosspolymer with tradename KSP-100 and KSP-101 available from ShinEtsu Chemical having an oil absorbency of more than 200 mf/100 g, and methyl methacrylate copolymer with tradename SA-GMP-0820 available from GANZ Chemical and surface treated by Miyoshi Kasei, Inc. having an oil absorbency of more than 100 mf/100 g. Typically, inclusion of oil absorbing powder for oil shine control may provide a composition with unfavorable spreadability performance. However, in the present invention, by including oil absorbing powder mainly in the second layer, the unfavorable spreadability performance can be improved. In a preferred example, the content level of an oil absorbing powder in the second layer is from about 1% to about 10%, more preferably from about 3% to about 5%.

Sebum Solidifying Powder

Sebum solidifying powder useful herein include those comprising a base substance which is coated with low crystalline zinc oxide, amorphous zinc oxide, or mixtures thereof, wherein the zinc oxide is from about 15% to about 25% by weight of the sebum solidifying powder. The base substance may be any organic or inorganic substances that are useful for cosmetic use, including those listed below under "Pigment Powder Component". The sebum solidifying powder herein can be suitably made according to the methods disclosed in US 2002/0031534 A1, herein incorporated by reference. The sebum solidifying powder may be surface treated. The sebum solidifying powder useful herein have the ability to solidify sebum, i.e., are effective in adsorbing free fatty acid, diglyceride, and triglyceride, and solidifying them by forming zinc salts thereof, such that a film is formed within about 30 minutes. Moreover, the originally glossy sebum changes appearance into a matte film. Such capability can be distinguished from other oil absorbing powder, which are not selective in the type of oil to be absorbed, and do not form a film after absorbing oil, thus may leave glossy gels and pastes after absorbing the sebum. Change in appearance provides a noticeable signal to the user that sebum has been controlled. Sebum solidifying effect may be conveniently measured by mixing a certain amount of powder with a certain amount of artificial sebum, mixing for a certain period of time, and allowing standing until solidified or showing matte appearance. The time taken for the mixture to solidify or to change appearance is recorded. The shorter the time taken to solidify or change appearance, the higher the solidifying effect is of the powder.

Commercially available sebum solidifying powder useful herein includes mica coated with hydroxyapatite, 20% zinc oxide with tradename PLV-20, and the same powder surface treated with methicone with tradename SI-PLV-20, both available from Miyoshi Kasei, Inc. Typically, inclusion of sebum solidifying powder for oil shine control may provide a composition with unfavorable spreadability performance. However, in the present invention, by including sebum solidifying powder mainly in the second layer, the unfavorable spreadability performance can be improved. In a preferred example, the content level of sebum solidifying powder in the second layer is from about 0.2% to about 10%, preferably from about 1% to about 7%.

Methods of Treatment

Various methods of treatment, application, regulation, or improvement may utilize the aforementioned compositions. Application of the present compositions can occur on any skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, application may be on a facial skin surface including the forehead, perioral, chin, periorbital, nose, and/or cheek skin surfaces.

Many regimens exist for the application of the composition to the skin. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before going out in public.

The step of applying the composition to the skin may be done by localized application to an area that contains wrinkles. In reference to application of the composition, the term "localized", "local", or "locally" mean that the composition is delivered the targeted area (such as an area of skin containing wrinkles) while minimizing delivery to skin surface not requiring treatment. The composition may be applied and lightly massaged into the skin. It is recognized that localized application does allow for a reasonable amount of the composition to be applied to areas adjacent the wrinkles to be treated (i.e., the composition is unlikely to be applied or to remain within the boundary of the wrinkles without some spreading). The form of the composition or the dermatologically acceptable carrier should be selected to facilitate localized application. While certain embodiments of the present invention contemplate applying a composition locally to a wrinkled area, it will be appreciated that compositions of the present invention can be applied more generally or broadly to one or more facial skin surfaces to reduce the appearance of wrinkles within those facial skin regions. Likewise, the compositions of the present invention can be applied as a continuous film, or in patterns. Striations, patterned spots or random application of the compositions may be desirable. Applicators, as described below, may be beneficial assisting in patterned deposition.

The regimen may optionally begin with a cleansing step. The consumer can wash her face with a suitable cleanser (e.g., Olay Purifying Mud Lathering Cleanser, available from The Procter & Gamble Company, Cincinnati, Ohio), and gently dry her skin with a towel. Another optional step to the treatment regimens of this invention include applying a moisturizer, examples of which are given below in Table 3 and are commercially available (e.g., Olay Natural White UV Moisturizing Lotion SPF 15, available from The Procter & Gamble Company, Cincinnati, Ohio). The moisturizer can be applied to the skin before the skin smoothing composition, after the skin smoothing composition, or both. This moisturizer may or may not contain oils or pigment. Another optional step to the treatment regimens of this invention include applying a make-up primer or color cosmetic examples of these are given and commercially available (e.g. Olay Simply Ageless Serum Primer, Covergirl Clean Liquid Makeup, Covergirl Simply Powder Foundation, available from The Procter & Gamble Company, Cincinnati, Ohio). As indicated in the examples, the color foundation step may be in a liquid, powder or transitional form. The extent of adhesion and contractile ability of the skin smoothing composition is dependent on the order of regimen product application to skin and compositions.

Applicators

In some embodiments, the composition may be delivered by a variety of applicators appropriate for localized and general application. By way of example, a suitable applicator may be a dropper and bottle that contains the composition. A pen-like wand with a housing that may contain the composition can also be used. The wand may comprise a handle, a stem, and an applicator head. The applicator head may comprise fibers, foam, cotton, a roller ball or any other suitable material that may releasably hold the composition. For example these may include, but are not limited to those described in published US Patent Application 2005/0025558 A1, to Raymond J. Severa, which application is assigned to Bonne Bell, Inc. or U.S. Pat. No. 5,851,079, to Richard L. Horstman, which application is assigned to The Procter & Gamble Co. One preferred foam for use in any applicator described herein is the gradient foam described in published US Patent Application 2009/0180826 A1, to Gordon Guay, which application is assigned to The Procter & Gamble Co.

A simple cotton swab can apply the composition locally to the wrinkled area. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to wrinkled areas having an approximate diameter between about 2 mm and about 20 mm and allowing for a dosed amount of the composition of between about 0.01 to about 2 mg/cm$^2$ or between about 0.1 to about 1 mg/cm$^2$. Thickness of the applied film can be measured or calculated based on the application are and application dose given directly above.

A narrow-tip tube with a body to hold the composition and a narrow dispensing tip may also be used. This embodiment may be considered a pre-loaded dropper. The composition may be stored within the body and dispensed through the pointed tip.

While some methods described herein contemplate applying the compositions of the present invention with an applicator, it will be appreciated that applicators are not required and the compositions of the present invention can also be applied directly by using one's finger or in other conventional manners.

EXAMPLES

Tables 1 and 2 below give two Examples according to the present invention.

TABLE 1

| Trade Name | General Description | As Added | Actual % |
|---|---|---|---|
| Water | Water | QS | QS |
| Hybridur 875 Polymer Dispersion (40% polymer solids in water) | Skin Tightener | 37.500 | 15.000 |
| Carbopol Ultrez 10 Polymer | Thickener | 1.000 | 1.000 |
| Niacinamide | Moisturizer | 0.500 | 0.500 |
| Petrolatum | Moisturizer | 1.000 | 1.000 |
| Fragrance | Fragrance | 0.100 | 0.100 |
| Ethanol | Solvent | 10.000 | 10.000 |
| Sodium Hyaluronate | Moisturizer | 1.000 | 1.000 |
| Glycerine | Humectant | 5.000 | 5.000 |
| Glydant Plus Liquid | Preservative | 0.320 | 0.320 |

TABLE 2

| Trade Name | General Description | As Added | Actual % |
|---|---|---|---|
| Water | Water | QS | QS |
| Hybridur 875 Polymer Dispersion (40% polymer solids in water) | Skin Tightener | 12.500 | 5.000 |
| Carbopol Ultrez 10 Polymer | Thickener | 0.360 | 0.360 |
| Glycerin USP 99.7% | Moisturizer | 1.000 | 1.000 |
| Xanthan Gum | Thickener | 1.000 | 1.000 |
| Glydant Plus Liquid | Preservative | 0.160 | 0.160 |

Example 3 below shows a comparative example intended to highlight the improvement provided by the combination of the polymeric film former and the claimed thickeners. Various thickeners were compared to the claimed class of polymeric, crosslinked acrylic acid, represented by the Carbopol family of thickeners. The comparative thickeners are discussed above under the heading of "Optional additional thickening agents". While many of these optional additional thickeners were tested, only the one that performed the best (but still well below the claimed thickeners) is shown in the FIGURE. The thickener that came closest to the performance of the thickeners is Sepigel 305, and the data is shown in the FIGURE.

Four compositions were made which varied only in the type of thickener and pH. Two compositions contained Carbopol and two contained Sepigel, each of the thickeners were formulated at approximately pH of 5.2 and 7.2. As can be seen, pH of 5.2 provides the optimal contraction regardless of thickener. The method for determining contraction is given below in the Test Method section. At both pHs, the Carbopol outperformed the Sepigel. Other thickeners were tested but none of them provided the level of contraction achieved by the Sepigel and Carbopol, so that data is not included.

Test Methods

To measure "contraction", as used herein, one measures the distance in inches (in) between two ends of a foam substrate after treatment with a skin smoothing composition. The foam substrate is a 3 mm thick open-cell polyurethane commercially available from Filtrona Porous Technologies as Medisponge 50 PW (the low strain or Young's modulus of this foam is 38.248 kPa) cut to 1×4 cm. In a 70° F.+/−2° C., 40%+/−2% relative humidity environment, with the foam substrate on a Teflon coated surface, 150 µL of the skin smoothing composition is dotted evenly atop the substrate, then lightly (~30 g pressure) spread across the substrate to cover the entire surface. The treated substrate is then allowed to dry 24 hours in this constant temperature/humidity environment. Then the projected distance between the ends of the foam substrate is measured with a ruler in inches. This procedure is performed in replicates of 3 or more and the values averaged.

The identical procedure detailed in the previous paragraph is also performed simultaneously with the Example 5 formulation. This data is used to normalize foam lot variability differences.

Then the following math is performed: "Contraction"= $[1.6-(D_{sample}-D_{Example\ 5})/1.6]*100$, where $D_{sample}$ is the projected distance in inches of the sample of interest, and $D_{Example\ 5}$ is the projected distance in inches of Example 5. In this calculation the the value 1.6 is used because it is the distance in inches of a foam strip devoid of contraction. Values greater than 100% indicate the sample has greater contraction than our reference point, Example 5; values less than 100% indicate the sample has less contraction than Example 5.

To measure the "loss of contraction," as used herein, one measures the distance in inches (in) between two ends of a foam substrate following treatment with a skin smoothing composition then repeated physical manipulation thereof. The treated foam substrates of the "contraction" method (described above) are repeatedly pressed into a flat orientation to determine the "loss of contraction". Subsequent to measuring "contraction", in a 70° F.+/−2° C., 40%+/−2% relative humidity environment, the treated foam substrates are placed singly, flat, between two glass microscope slides, then a 305 g weight applied atop the upper glass slide for 10 seconds. The weight is removed for 10 seconds, then applied and removed in the same 10 second increments 2 additional cycles. The foam substrate is removed from the glass slides, set on a Teflon-coated surface, then after 10 minutes, the projected distance in inches (in) between two ends of a foam substrate measured using a ruler. This projected distance is called $D_{sample\ post-insult}$. The "Loss of Contraction"= $(D_{sample}-D_{sample\ post-insult})/D_{sample}$.

To measure "Whiteness", as used herein, one measures the opacity or lightness/darkness intensity. For the purposes of the present invention, color is defined according to a value on the CIELAB color system, which is based on the XYZ color system, defined by the Commission Internationale de l'Eclairage (CIE system) to provide a manner of objectively representing perceived color and color differences. X, Y and Z can be expressed in a variety of manners, or "scales," one of which is the Hunter scale. The Hunter scale has three variables, L, a, and b, which correlate mathematically to X, Y and Z, as described by Robertson, A. R. in "The CIE 1976 Color Difference Formulas," *Color Research Applications*, vol. 2, pp. 7-11 (1977). The compositions of the present invention may be analyzed with a Microflash integrating sphere spectrophotometer from DataColor International, Lawrenceville, N.J., USA, which generates values for L, a, and b. The value for "a" correlates to a value along the red-green (horizontal) axis, and the value for "b" correlates to a value along the blue-yellow (vertical) axis. For example, a blue-colored sample will have a negative b-value, whereas a red-colored sample will have a positive a-value. A more positive or negative value represents a more intense color. The value for "L" is an indicator of lightness and/or darkness, and correlates to a value along the z-axis, which is perpendicular to both the horizontal and vertical axes. An "L" of 0 is black and 100 a diffuse white. It is "L" that is used as a determinant of the film's "whiteness."

To measure the whiteness of a film it must first be drawn. Herein, "drawn" means that the composition is applied onto at least a portion of the black portion of an opacity chart (Form 2A, Leneta Company of Manwah, N.J. or the equivalent thereof, of which the top half is black and the bottom half is white) and spread into a film having a thickness of approximately 0.003 inches using a film applicator (e.g., as commercially available from BYK Gardner of Columbia, Md., or the equivalent thereof). The whiteness is then measured on the black portion of the opacity chart after the drawn film is allowed to dry for 24 hours under conditions of 70° F.+/−2° C., 40%+/−2% relative humidity using a spectrophotometer (e.g., Microflash integrating sphere spectrophotometer, specular-reflections included). Again, whiteness is used in reference to the "L" value of the drawn films. A higher number indicates the product looks white against the black background, while a lower number indicates the product is less white and/or more translucent, allowing greater visibility of the black background. Whiteness determinations are performed in replicates of 2.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin smoothing composition comprising:
 a) from about 0.5 to about 10%, by weight, of a copolymer of neopentyl glycol/adipic acid/4,4'-methylenebis(cyclohexyl isocyanate)/dimethylolpropanoic acid and of polymethyl methacrylate;
 b) from about 0.1% to about 5%, by weight, of a thickener comprising homopolymers of acrylic acid crosslinked with a cross linker selected from the group consisting of an allyl ether pentaerythritol, allyl ether of sucrose, allyl ether of propylene and mixtures thereof;
 c) from about 10 to 98% water; and
 d) wherein said composition has a pH of about 5.2.

2. The composition of claim 1, further comprising from about 1% to about 20%, by weight of a plasticizer, wherein the plasticizer is an alkyl mono-glycol or di-glycol.

3. The composition of claim 2, wherein the plasticizer structure contains 3 to 5 carbon atoms.

4. The composition of claim 2, wherein the plasticizer is propylene glycol.

5. The composition of claim 1, further comprising at least one polysaccharide thickener.

6. The composition of claim 5, wherein the polysaccharide thickener is xanthan gum.

7. The composition of claim 1, further comprising from about 0.001% to about 5% of a particulate material selected from the group consisting of colored and uncolored pigments, interference pigments, inorganic powders, organic powders, composite powders, optical brightener particles, and mixtures thereof.

8. The composition of claim 1, further comprising at least one skin care active.

9. The composition of claim 8, wherein the skin care active is selected from the group consisting of vitamin B compounds, vitamin C compounds, vitamin E compounds, peptides, sugar amines, natural botanical extract, oil control agents, skin lightening agents, and mixtures thereof.

10. The composition of claim 8, wherein the skin care active is selected from the group consisting of niacinamide, palmitoyl-lysine-threonine, palmitoyl-lysine-threonine-threonine-lysine-serine, N-acetyl-D-glucosamine, salicylic acid, dehydroacetic acid, sodium dehydroacetate, hexamidine compounds, and mixtures thereof.

11. A kit comprising a first composition and a second composition, wherein:
 i) the first composition is a skin smoothing composition in the form of a water gel or oil-in-water emulsion and the skin smoothing composition comprises:
  a. from about 0.5 to about 10%, by weight, of an a copolymer of neopentyl glycol/adipic acid/4,4'-methylenebis(cyclohexyl isocyanate)/dimethylolpropanoic acid and of polymethyl methacrylate;
  b. from about 0.1% to about 5%, by weight, of thickener comprising homopolymers of acrylic acid crosslinked with a cross linker selected from the group consisting of an allyl ether pentaerythritol, allyl ether of sucrose, allyl ether of propylene and mixtures thereof;
  c. from about 10 to 98% water; and,
  d. wherein said first composition has a pH of about 5.2; and
 ii) the second composition comprises at least one component selected from the group consisting of an oil-in-water emulsion, water-in-oil emulsion, thickened water gel, thickened oil phase, encapsulated oil phase, solid oil phase, and mixtures thereof, wherein the second composition is a skin care composition or colored cosmetic composition; and
 iii) instructions for complying with a regimen to provide a benefit to keratinous tissue.

12. The kit of claim 11, further comprising at least one additional component selected from the group consisting applicators, delivery implements, or powered delivery devices to deliver the personal care composition to skin.

* * * * *